United States Patent [19]
Schaefer et al.

[11] Patent Number: 5,490,520
[45] Date of Patent: Feb. 13, 1996

[54] DENTAL APPLICANCE FOR TREATING BRUXISM

[75] Inventors: Donald W. Schaefer, deceased, late of Madison, Wis., by Katherine M. Bach, personal representative; Melvin P. Siedband, Madison, Wis.

[73] Assignee: Schaefer Partnership, Eau Claire, Wis.

[21] Appl. No.: 129,225

[22] Filed: Sep. 27, 1993

[51] Int. Cl.$^6$ ................................ A61F 5/56; A61C 5/14
[52] U.S. Cl. ........................................ 128/848; 128/861
[58] Field of Search .......................... 128/848, 859–862, 128/62 A, 724, 733, 774, 777; 602/902; 340/573, 574, 575, 626, 665, 668

[56] References Cited

U.S. PATENT DOCUMENTS

| | | | |
|---|---|---|---|
| 3,998,209 | 12/1976 | Macvaugh | 128/848 |
| 4,519,400 | 5/1985 | Brenman | 128/787 |
| 4,593,686 | 6/1986 | Lloyd | 128/848 |
| 4,669,477 | 6/1987 | Ober. | 128/782 |
| 4,788,533 | 11/1988 | Meguignon | 600/28 |
| 4,830,008 | 5/1989 | Meer | 128/721 |
| 5,123,425 | 6/1992 | Shannon | 128/848 |
| 5,190,053 | 3/1993 | Meer | 128/787 |
| 5,265,624 | 11/1993 | Bowman | 128/848 |
| 5,284,161 | 2/1994 | Karell | 128/848 |

*Primary Examiner*—Michael A. Brown
*Attorney, Agent, or Firm*—Foley & Lardner

[57] ABSTRACT

A dental appliance for treating bruxism is provided which, according to one aspect of the invention, has a mouthpiece containing an electric source, electrodes, and circuitry connecting the source to the electrodes, and circuitry connecting the source to the electrodes. The electrodes are disposed to contact an interior surface of the wearer's mouth to conduct electric stimuli to the mouth. Included in the electronic circuitry, are sensors which trigger the flow of electric current from the source to the electrodes when squeezed together by the wearer's teeth.

16 Claims, 2 Drawing Sheets

5,490,520

DENTAL APPLIANCE FOR TREATING BRUXISM

TECHNICAL FIELD

This invention relates to dental appliances, particularly to mouthpieces used to treat bruxing.

BACKGROUND OF THE INVENTION

Many people, for reasons not clearly understood, grind their teeth at night while sleeping. The usual complaints related by this group of people are soreness in joints, facial muscles, and neck muscles, headaches, clicking of the jaw, earaches, etc. Most of these people seek help from their dentist or physician who cite headache disorders, cranial neuralgia and facial pain as the most common symptoms. This grinding of the teeth is called bruxing. Commonly, the grinding of the teeth takes place during the night and the condition is referred to as nocturnal bruxism. Such clenching and grinding of the teeth can also lead to the onset of temporomandibular joint syndrome or temporomandibular disfunction referred to as TMJ syndrome or TMD.

In spite of the fact that there has been an explosion of interest and research regarding bruxism and TMJ disorders in the past ten years, the most common treatment continues to be the "night splint" usually prescribed by dentists. A night splint is a plastic dental appliance made from a model of the patient's teeth and is designed to fit firmly on either the upper or lower teeth. The night splint is usually fitted to the upper teeth and is somewhat similar to a boxer's mouthpiece.

In general, most attempts to relieve people of the TMJ syndrome or its precursor "nocturnal bruxism" have failed. People fitted with a night splint usually grind through the appliance over time and are required to have another made. Such an appliance may prevent further deterioration of the teeth and relieve pressure on the joints but does little or nothing to prevent the grinding process.

Some inventions have attempted to incorporate the use of electronic stimuli in conjunction with various dental appliances. In both Tepper, U.S. Pat. No. 3,259,129, and Tepper, U.S. Pat. No. 3,277,892, a dental appliance for correcting tongue thrust problems is disclosed. Each of these patents describes a dental retainer including a source of electricity connected to a pair of electrodes embedded in the retainer. When the wearer's tongue is improperly thrust forward into contact with the electrodes, an electrical stimulus is imparted to the wearer's tongue. The Tepper devices, however, do nothing to prevent the wearer from grinding his teeth.

Other related dental appliances are disclosed in Dellinger, U.S. Pat. No. 4,396,373, issued Aug. 2, 1983, Smiley et al., U.S. Pat. No. 4,484,895, issued Nov. 27, 1984, and Lauks et al., U.S. Pat. No. 4,629,424, issued Dec. 16, 1986. None of these devices uses electronic stimuli to prevent bruxism.

The present invention addresses the foregoing drawbacks and disadvantages of known dental appliances.

SUMMARY OF THE INVENTION

The present invention provides a dental appliance which, according to one aspect of the invention, has a mouthpiece, a source of electrical current affixed to the mouthpiece, and an electrode affixed to the mouthpiece. The electrode is disposed to contact an interior surface of the wearer's mouth when the mouthpiece is positioned therein. An electric circuit connects the source and the electrode so an electric current is selectively provided between the source and the electrode when the wearer's upper and lower teeth contact. The electric stimuli provided by the electrode causes the wearer to unclench his teeth.

BRIEF DESCRIPTION OF THE DRAWINGS

The invention will hereafter be described with reference to the accompanying drawing, wherein like numerals denote like elements and.

DETAILED DESCRIPTION OF PREFERRED EMBODIMENTS

Figure 1:
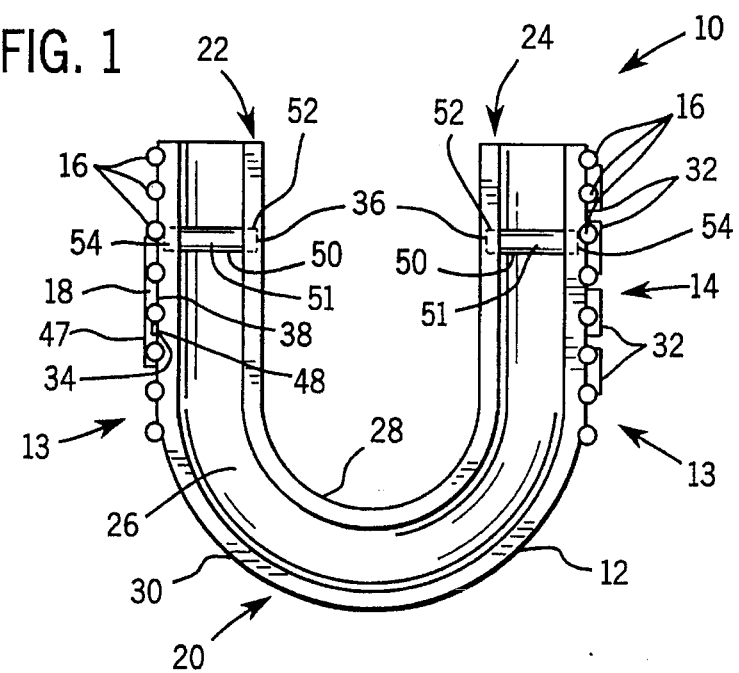
FIG. 1 is a top plan view of a dental appliance according to the invention.
Figure 2:
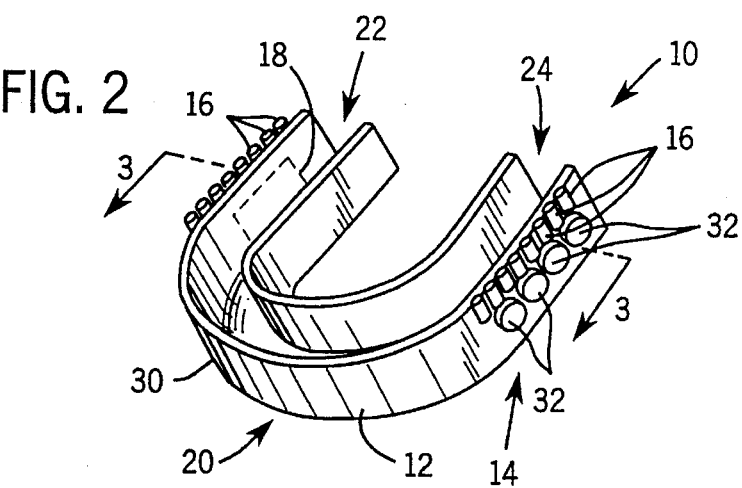
FIG. 2 is a perspective view of the dental appliance shown in FIG. 1.
Figure 3:
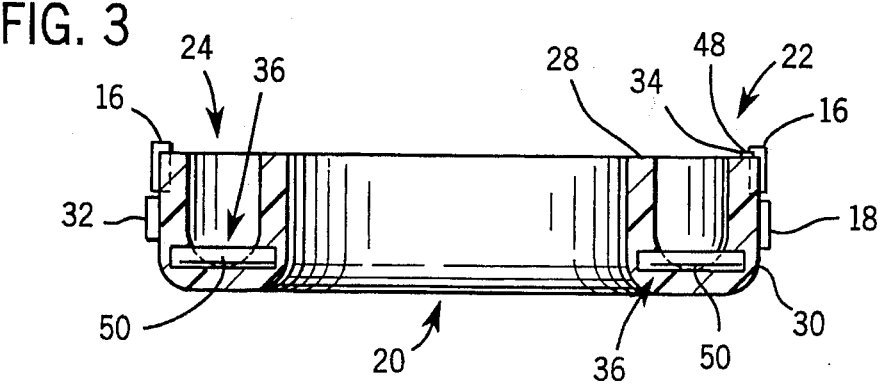
FIG. 3 is a cross-sectional view taken generally along line 3—3 in FIG. 2.

Referring generally to FIGS. 1 through 3, a dental appliance 10 according to the invention is comprised of a mouthpiece 12 and an associated electrical stimulus subassembly, designated generally as 13. The electrical stimulus subassembly is borne upon and affixed to the mouthpiece 12, and is comprised of a power source 14, electrodes 16 disposed to contact an interior surface of the wearer's mouth when dental appliance 10 is positioned in the wearer's mouth, and an electric circuit 18 connected between power source 14 and electrodes 16.

Mouthpiece 12 can be one of a variety of types which are well known in the art. Typically, a full palate dental retainer, which may be of the Hawley type, or a similar splint type, or a self-contained lower jaw splint type retainer, may be used. Mouthpiece 12 is preferably made of a plastic substrate which is molded from a dental model of the patient's teeth.

In a preferred embodiment, mouthpiece 12 has a generally horseshoe shape and comprises a curved front portion 20, a left leg 22 and a right leg 24. Left leg 22 and right leg 24 are integral with curved front portion 20 and would generally follow the contours of the wearer's upper or lower teeth. Mouthpiece 12 is configured to fit over the wearer's teeth and thus further includes a base 26 generally disposed to abut the chewing surface of the teeth. Extending from base 26 and disposed behind and in front of the wearer's teeth are an inner wall 28 and an outer wall 30, respectively. As shown in FIG. 3, base 26, inner wall 28, and outer wall 30 also form a U-shape when taken in cross-section.

Power source 14 includes battery cells 32 which are embedded in outer wall 30 of mouthpiece 12. In a preferred embodiment, power source 14 has four lithium button cells which are connected in series. Each battery cell 32 is preferably a dry cell rated at approximately 3 V. When dental appliance 10 is being used, the battery life is 150 hours or more, while the shelf life of the batteries, under zero current flow conditions, can be several years.

Electrodes 16 are preferably metal or plastic conductors embedded in outer wall 30 of both left leg 22 and right leg 24. Electrodes 16 are embedded in mouthpiece 12 to contact an interior surface of the wearer's mouth when mouthpiece 12 is properly inserted. In a preferred embodiment, electrodes 16 contact the wearer's gum line, i.e., the tissue that surrounds the necks of teeth and covers the alveolar parts of the jaws. Electrodes 16 are preferably arranged in a linear array along outer wall 30 of legs 22 and 24 to contact the gum line in a plurality of locations.

Electronic circuit 18 is connected between power source 14 and electrodes 16 and selectively conducts electricity between the power source and the electrodes when the individual wearing the dental appliance brings his upper and lower jaws together into a closed position. Electronic circuit 18 is preferably powered by battery cells 32 and generally comprises an ON/OFF switch 34, a sensor 36, and at least one flexible printed circuit board 38. Circuit 18 also includes an oscillator 40 connected to sensor 36 through an inhibit circuit 42 all mounted on circuit board 38. In the most preferred embodiment, circuit board 38 is wrapped over the exterior surface of outer wall 30 on both left leg 22 and right leg 24, cemented in place and sealed with a plastic film 47. In certain applications, a portion of the circuit board may be obviated by spot welding connections directly to the cells and wiring them to a smaller circuit board mounted on either leg, shown for example on left leg 22 in FIG. 2.

Generally, ON/OFF switch 34 energizes circuit 18 when it is closed or turned on. ON/OFF switch 34 is preferably a dynamic switch such as a field effect transistor (FET) connected to contacts 48 which have exposed ends extending through outer wall 30. The FET is biased to a nonconducting state until a conductive fluid, such as saliva, creates a conductive path between contacts 48 and turns it on. When dental appliance 10 is removed from the wearer's mouth and dried, the conductive path between contacts 48 is broken thus returning switch 34 to its normally open or off position. When switch 34 is closed, current from power source 14 energizes electronic circuit 18. The current flows from power source 14 and effectively short-circuits through sensor 36, at least until pressure is exerted against sensor 36. Once adequate pressure is exerted, oscillator 40 provides controlled electrical pulses or stimuli to electrodes 16. However, if switch 34 is in the open or off position, no current is allowed to flow from electric power source 14.

Figure 4:
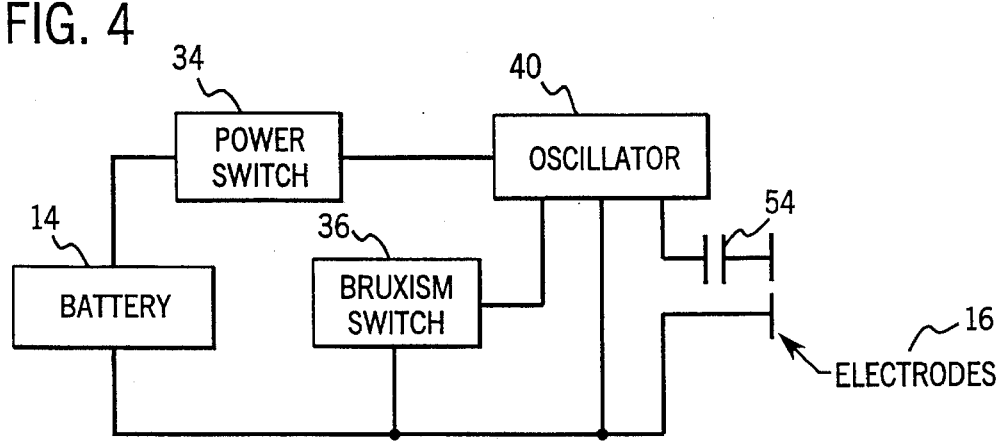
FIG. 4 is a block diagram of the circuit.

Sensor 36 preferably functions as a dynamic switch and comprises a small diameter flexible tube 50 filled with a dilute saline solution 51. One or more tubes may be used. Tube or tubes 50 are made from a resilient, nonporous flexible rubber or plastic which is deformable under normal external pressure. Tube 50 can have different volumes or different levels of stiffness to alter its sensitivity to bruxing force. In a preferred embodiment, tube 50 extends across base 26 and has its inner end 52 and its outer end 54 embedded in inner wall 28 and outer wall 30, respectively. Tube 50 is thus disposed axially across leg 22 or 24 or both so that flexible tube 50 is squeezed together and collapses as the wearer bites down. When sufficient bruxing pressure is applied to tube 50, it is deformed to an extent that interrupts the continuous conductive fluid path extending through tube 50. Current can then no longer flow through saline solution 51 of sensor 36. Under these conditions, electronic circuit 18 is no longer short-circuited through tube 50. This allows battery cells 32 to power oscillator 40 which feeds pulses of energy via an isolation capacitor 54 to the electrodes 16 disposed in the wearer's mouth (see FIG. 4). This electrical stimulation is detected by the trigeminal which supplies the face and upper and lower jaw with sensory nerves along the facial and the vagus. The ophthalmic and the maxillary divisions of the trigeminal are purely sensory, and the mandibular division contains motor fibers to the muscles of mastication as well.

The bruxing pressure on tube 50 opens electrical circuit 18 to allow a small electric shock to be felt at the gum line stimulating the proprioception of the trigeminal efferent branch to cause the release of tension or contraction of the masticator muscles via the efferent branch of the trigeminal by reflex reaction. This relaxes the jaw musculature much like that experienced when one bites down a hard kernel of popcorn, causing a reflex reaction. In some applications, a reasonable shock level may be provided by 6 to 9 volts.

Bruxing forces could be sufficient to damage tubes 50 in certain situations. Therefore, in the preferred embodiment, the resilient tubes 50 will be fitted into the base of the appliance so they are only partially exposed to the bruxing forces. For instance, the round tube 50 could be positioned in a semi-circular trough so the bruxing force would be sufficient to interrupt the circuit without shearing or damaging the tube.

Figure 5:
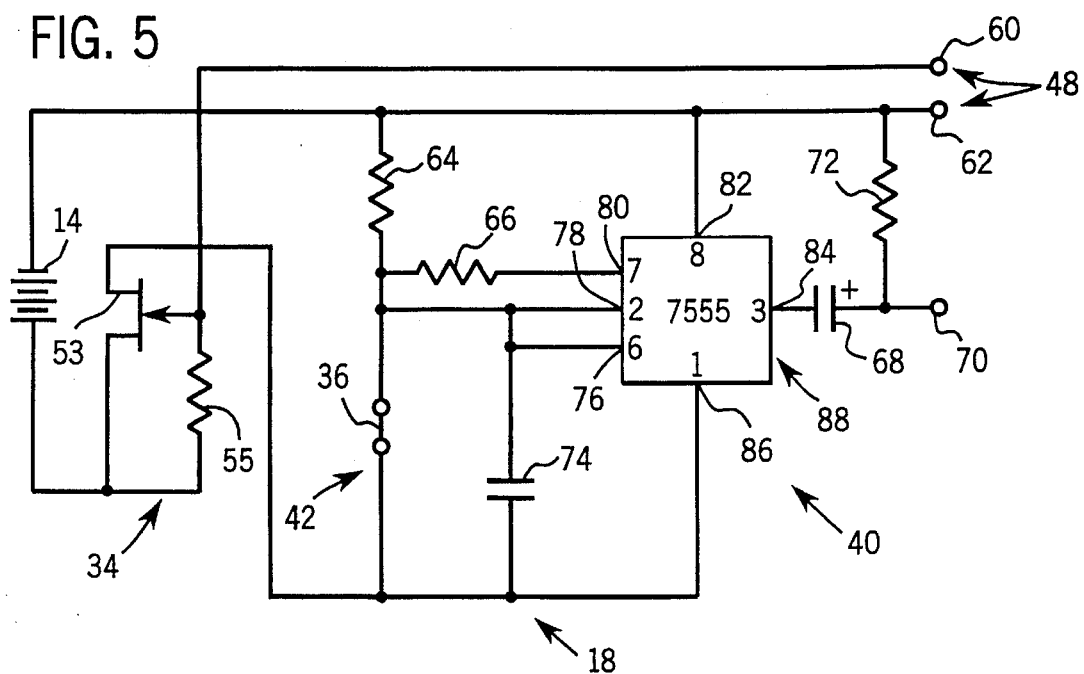
FIG. 5 is a circuit diagram showing the preferred electronic circuit used in the invention.

An exemplary embodiment of electronic circuit 18 will now be described in detail. Referring to FIG. 5, contacts 48 include a first contact 60, which is coupled to the anode of power source 14, and a second contact 62, which is coupled to switch 34. Switch 34 generally includes a transistor 53, and a resistor 55. The gate of transistor 53 is directly coupled to contact 62 and coupled to ground through resistor 55. The drain of transistor 53 is coupled to ground, and the source of transistor 53 is coupled to sensor 36, a capacitor 74, and a timing circuit 88.

When contact 60 is not electrically coupled to contact 62, switch 34 is OFF. In this configuration, an open circuit exists between the anode of power source 14 and the gate of transistor 53. Since no potential is applied to the gate of transistor 53, the source and drain of transistor 53 remain electrically isolated.

Switch 34 is ON when contact 60 is electrically coupled to contact 62 by conducting fluid, such as saliva or other moisture in a wearer's mouth. In this configuration, a circuit is completed between the anode of power source 14 and the gate of transistor 53, thus applying a potential at the gate of transistor 53 which allows current to flow from the source of transistor 53 to the drain of transistor 53.

Oscillator 40 generally includes timing circuit 88, a plurality of resistors 64, 66, and 72, a capacitor 68, and capacitor 74. Timing circuit 88, which may suitably includes a 7555 timing chip, has a plurality of terminals, 76, 78, 80, 82, 84 and 86. Terminal 80 is the discharge terminal of timing circuit 88 and is coupled to the anode of power source 14 through resistors 64 and 66, and to capacitor 74 through resistor 66. Terminal 78 is the trigger terminal of timing circuit 88 and terminal 76 is the threshold terminal of timing circuit 88. Terminals 76 and 78 are coupled to the anode of power source 14 through resistor 64 and to capacitor 74. Terminal 82 is coupled to the anode of power source 14 and terminal 86 of timing circuit 88 is coupled to ground through switch 34. Terminal 84 is the output terminal of timing circuit 88 and is coupled to the anode of power source 14 through capacitor 68 and resistor 72 and to capacitor 68. Capacitor 68 is coupled to electrodes 16 by a contact 70 and to the anode of power source 14 through resistor 72.

When switch 34 is ON and sensor 36 is rendered non-conductive by pressure being exerted thereon, as discussed above, oscillator 40 is activated. In this configuration, the voltage at threshold terminal 76 is initially low, driving output terminal 84 high. Also, the voltage across capacitor 74, initially zero volts, increases as capacitor 74, no longer short-circuited by sensor switch 36, charges through resistor 64. The rate at which capacitor 74 is charged depends on the capacitance of capacitor 74 and the resistance of resistor 64. The voltage at terminal 84 remains high until the voltage at threshold terminal 74 reaches ⅔ the input voltage at terminal 82 (Vcc).

When the voltage at threshold terminal 76 reaches ⅔ Vcc, the voltage at output terminal 84 is driven low. Also, discharge terminal 80 is tied to ground, causing capacitor 74 to discharge through resistor 66. The rate of discharge is determined by the capacitance of capacitor 74 and the resistance of resistor 66. The voltage at output terminal 84 remains low and capacitor 74 continues to discharge until the voltage at trigger terminal 78 reaches ⅓ Vcc.

When the voltage at trigger terminal 78 falls below ⅓ Vcc, the output at terminal 84 is driven high. Also, the circuit between discharge terminal 80 and ground is broken, causing capacitor 74 to recharge once again through resistor 64. Thus, when switch 34 is ON, and sensor switch 36 is nonconductive, the voltage at output terminal 84 will oscillate between high and low and the voltage across capacitor 74 will oscillate between ⅓ Vcc and ⅔ Vcc.

As described above, the voltage at output terminal 84 continuously oscillates between high and low. Initially, the voltage at output terminal 84, contact 70, and contact 62 is high, making the potential across capacitor 68 zero. When oscillator 40 is activated and output terminal 84 goes low, the voltage at contact 70 also goes low as the potential across a capacitor does not change instantaneously. Capacitor 68 begins to charge as current starts to flow from the high potential at contact 62 to the low potential at contact 70 through resistor 72 and the conductive moisture in the wearer's mouth. The rate at which capacitor 68 is charged depends upon the resistance of both resistor 72 and the capacitance of capacitor 68. As output terminal 84 goes high, the voltage at contact 70 is driven above Vcc to maintain the instantaneous potential across capacitor 68. The resulting current flow from contact 70 to contact 62 through resistor 72 and the moisture in the wearer's mouth discharges capacitor 68. This process is continuously repeated as output terminal 84 oscillates between high and low while timing circuit 88 is activated.

Sensor 36 connects one side of capacitor 74 to the other. As discussed above, when bruxing pressure is exerted against sensor 36, sensor 36 does not conduct, and when pressure is not exerted against sensor 36, sensor 36 does conduct. Thus, when pressure is not exerted against sensor 36, capacitor 74 is short circuited and cannot charge, inhibiting circuit 18 from operation and allowing no potential across capacitor 74. Since capacitor 74 cannot charge, the voltage at terminals 76 and 78 remain constant and timing circuit 88 remains inactive. In this configuration, oscillator 40 is inhibited and output terminal 84 will remain high.

It will be understood that the foregoing description is of a preferred exemplary embodiment of this invention, and that the invention is not limited to the specific forms shown. For example, different configurations and materials may be used for mouthpiece 12, electronic circuit 18 may use different components than those listed and different numbers of tubes 50 can be used in sensor 36. These and other modifications may be made in the design and arrangement of the elements without departing from the scope of the invention as expressed in the amended claims.

What is claimed is:

1. A dental appliance for treating bruxism, comprising:
   a mouthpiece configured to fit within the mouth of a wearer, the mouthpiece having a wall configured to receive a current source;
   an electrode configured and disposed to contact an interior surface of the wearer's mouth when the mouthpiece is placed therein;
   an electric circuit mounted to the mouthpiece, the electric circuit being configured to connect the current source and the electrode, wherein the electric circuit is configured to selectively provide current flow between the current source and the electrode when the wearer's upper and lower jaws are brought together with bruxing force; and
   wherein said electric circuit comprises a sensor, disposed on the mouthpiece, for sensing the application of bruxing force.

2. The dental appliance of claim 1 wherein the electric circuit comprises a power switch responsive to the application of a conductive fluid.

3. The dental appliance of claim 2, wherein said switch is a field effect transistor having contacts which turn on the field effect transistor and allow current to flow from the source when the contacts are electrically connected by a conductive fluid.

4. The dental appliance of claim 1, wherein the source has a battery of cells.

5. The dental appliance of claim 1, wherein the electrode is at least partially embedded in the mouthpiece.

6. The dental appliance of claim 5, wherein the electronic circuit is at least partially embedded in the mouthpiece.

7. The dental alliance of claim 6, wherein the power source is at least partially embedded in the mouthpiece.

8. A dental appliance for treating bruxism, comprising:
   a mouthpiece configured to fit within the mouth of a wearer;
   a current source operatively associated with said mouthpiece;
   an electrode configured and disposed to contact an interior surface of the wearer's mount when the mouthpiece is placed therein; and
   an electric circuit connecting the source and the electrode, wherein the electric circuit selectively provides current flow between the source and the electrode when the wearer's upper and lower jaws are brought together with bruxing force, wherein said electric circuit comprises a sensor, disposed on the mouthpiece, for sensing the application of bruxing force wherein said sensor comprises a deformable tube through which electric current can flow when the tube is not deformed and through which electric current cannot flow when the tube is deformed upon application of a threshold bruxing force.

9. A dental appliance for treating bruxism, comprising:
   a mouthpiece configured to fit within the mouth of a wearer;
   a first contact and a second contact affixed to the mouthpiece and connected to a battery through an electronic circuit, the first and second contacts being disposed operative engagement with an interior surface of the wearer's mouth when the mouthpiece is placed therein, wherein said electronic circuit is mounted to the mouthpiece and configured to provide an electric pulse to the wearer's mouth when the mouthpiece is placed therein and the wearer's upper and lower jaws are brought together with bruxing force; and
   wherein the electronic circuit comprises a sensor attached to the mouthpiece having a conductance responsive to a threshold bruxing force.

10. The dental appliance of claim 9 wherein the electronic circuit further comprises:

a switch responsive to the presence of conductive fluid between the first and second contacts; and p1 a timing circuit responsive to the sensor and the switch, wherein the timing circuit provides an oscillating output voltage when the wearer's upper and lower jaws are brought together with a bruxing force and said fluid electrically couples the first and second contacts.

11. A dental appliance for treating bruxism, comprising:

a mouthpiece configured to fit within the mouth of a wearer;

a first contact and a second contact affixed to the mouthpiece and connected to a battery through an electronic circuit, the first and second contacts being disposed in operative engagement with an interior surface of the wearer's mouth when the mouthpiece is placed therein, wherein said electronic circuit provides an electric pulse to the wearer's mouth when the mouthpiece is placed therein and the wearer's upper and lower jaws are brought together with bruxing force, wherein the electronic circuit comprises a sensor having a conductance responsive to a threshold bruxing force, wherein the sensor comprises a deformable tube through which electric current can flow when the tube is not deformed and through which electric current cannot flow when the tube is deformed by bruxing force.

12. A dental appliance for treating bruxism, comprising:

a mouthpiece configured to fit within the mouth of a wearer;

a current source receiving area disposed on said mouthpiece and configured to receive a current source;

a dynamic switch, responsive to the application of a conductive fluid, in series with said current source for controlling whether current flows from said source;

an electrode configured and disposed to contact a gum line of the wearer's mouth when the mouthpiece is placed therein;

a sensor operatively associated with said mouthpiece, wherein said sensor is responsive to the application of a bruxing pressure; and means for providing electrical pulses to the electrodes when said sensor experiences pressure and said switch is closed.

13. The dental appliance of claim 12, wherein said means comprises an oscillator for controlling current flow to the electrodes, said oscillator being activated when the sensor is deformed by pressure between the upper and lower jaws of the wearer.

14. The dental appliance of claim 12, wherein said switch comprises a field effect transistor electrically connected to contacts, the field effect transistor being normally biased to a nonconducting state until moisture forms a conductive path between said contacts at which time said field effect transistor is biased to a conducting state allowing current to flow from said source and to energize said means.

15. A dental appliance for treating bruxism, comprising:

a mouthpiece configured to fit within the mouth of a wearer;

an associated electrical stimulus subassembly for providing electrical stimulus to the mouth of a wearer where the wearer's upper and lower jaws are brought together with bruxing force, wherein said associated electrical stimulus subassembly includes a dynamic sensor mounted to the mouthpiece and responsive to the application of a bruxing force.

16. The dental appliance of claim 15, wherein said associated electrical stimulus subassembly further comprise a switch responsive to the application of a conductive fluid.

* * * * *